United States Patent [19]

Tamatani et al.

[11] Patent Number: 5,893,999

[45] Date of Patent: *Apr. 13, 1999

[54] ULTRAFINE INORGANIC PHOSPHOR, SPECIFICALLY BINDING MATERIAL LABELED WITH THIS PHOSPHOR, AND DETECTION METHOD USING THIS SPECIFIC BINDING MATERIAL

[75] Inventors: Masaaki Tamatani, Fujisawa; Hirotami Koike, Hamura; Miwa Okumura, Kawasaki; Keiko Albessard, Yokohama; Naotoshi Matsuda, Machida, all of Japan

[73] Assignee: Kabushiki Kaisha Toshiba, Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/304,868

[22] Filed: Sep. 13, 1994

[30] Foreign Application Priority Data

Sep. 13, 1993 [JP] Japan ................. 5-227058

[51] Int. Cl.⁶ ............. C09K 11/08; C09K 11/54; C09K 11/55; C09K 11/77

[52] U.S. Cl. ............. 252/301.4 R; 252/301.4 S; 252/301.5; 252/301.6 R

[58] Field of Search ................. 436/525, 546; 530/391.3; 252/301.4 R, 301.5, 301.6 R, 301.4 S

[56] References Cited

U.S. PATENT DOCUMENTS

| | | |
|---|---|---|
| 3,338,841 | 8/1967 | Brixner . |
| 3,368,980 | 2/1968 | Avella et al. . |
| 3,437,432 | 4/1969 | Borchardt . |
| 3,449,258 | 6/1969 | Ropp et al. . |
| 3,848,068 | 11/1974 | Rice . |
| 4,610,857 | 9/1986 | Ogawa et al. . |
| 4,769,064 | 9/1988 | Buss et al. . |
| 5,043,265 | 8/1991 | Tanke et al. ................. 435/6 |

FOREIGN PATENT DOCUMENTS

| | | |
|---|---|---|
| 59-122950 | 7/1984 | Japan . |
| 4-310516 | 11/1992 | Japan . |

OTHER PUBLICATIONS

R. Bayliss et al., J. Materials Science, vol. 3, No. 3, pp. 229–238, May 1968.

C. Pickles et al., Amer. Ceramic Soc. Bull., vol. 62, No. 9, pp. 1004–1009, Sep. 1983.

T. Uchida et al., English abstract of Japanese patent JP 59-122950 (1991).

Denshikenbikyogakn (Electromicroscopy), p. 329, "Electron Microscopic Immuno–histochemistry", Y. Ibata, 1983.

Primary Examiner—Mary E. Ceperley
Attorney, Agent, or Firm—Oblon, Spivak, McClelland, Maier & Neustadt, P.C.

[57] ABSTRACT

A specific binding material labeled with an ultrafine inorganic phosphor 1 to 100 nm in particle size is disclosed. The composition of the ultrafine inorganic phosphor is one of $Ln_2O_3$:Re, $Ln_2O_2S$:Re, ZnO, $CaWO_4$, $MO.xAl_2O_3$:Eu, $Zn_2SiO_4$:Mn, and $LaPO_4$:Ce,Tb, wherein Ln represents at least one element selected from La, Gd, Lu, and Y, Re represents at least one element selected from lanthanide elements, M represents at least one element selected from alkali earth metals, and x represents a value from 0.5 to 15. This ultrafine inorganic phosphor is prepared by one of the following processes a process of evaporation in a gas including an RF thermal plasma process, dc plasma thermal spraying, sputtering, glass crystallization, a sol-gel process, precipitation including hydrothermal synthesis, and a spraying process. An antibody which reacts specifically with an antigen to be measured is labeled with this ultrafine inorganic phosphor and reacted with a specimen, and the unreacted material is removed. The antibody bound to the specimen is detected by quantitatively observing fluorescence emitted by the phosphor.

3 Claims, 3 Drawing Sheets

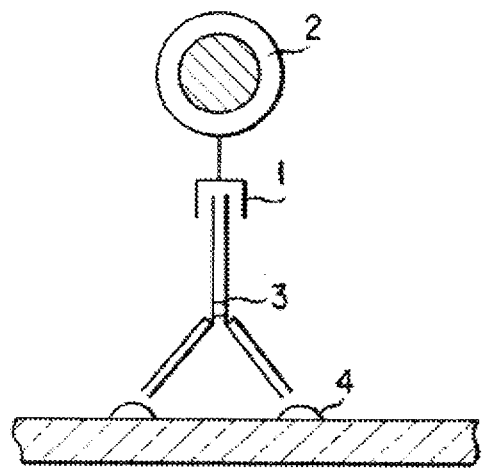
F I G. 1
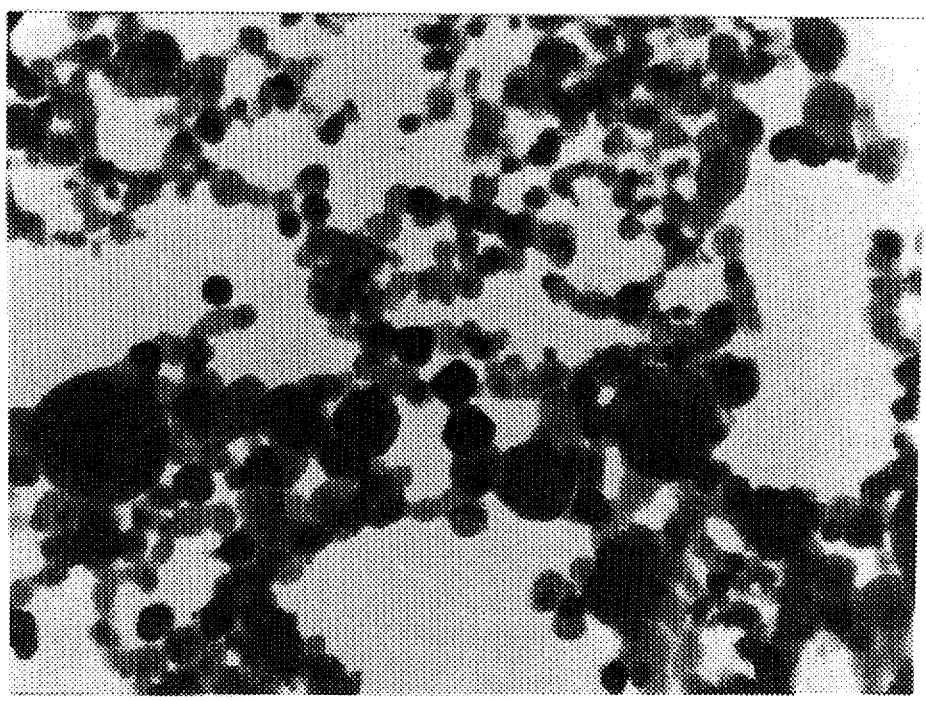
F I G. 2

ULTRAFINE INORGANIC PHOSPHOR, SPECIFICALLY BINDING MATERIAL LABELED WITH THIS PHOSPHOR, AND DETECTION METHOD USING THIS SPECIFIC BINDING MATERIAL

BACKGROUND OF THE INVENTION

1. Field of the Invention

The present invention relates to an ultrafine inorganic phosphor, a specifically binding material labeled with this phosphor, and a detection method using this specific binding material

2. Description of the Related Art

In the fields of medicine and biology, there is a method in which a fluorescent substance consisting of organic molecules is used as a label, and fluorescence emitted by irradiation of ultraviolet radiation is observed with an optical microscope or a photodetector. This method has been conventionally used in the studies of viruses or reactions of enzymes or in clinical examinations. Of the methods of this type, a fluorescent antibody method is well known. This method uses an antibody to which an organic phosphor which emits fluorescence is bonded. The antigen-antibody reaction is compared to a keyhole and key relationship since the reaction has a very high selectivity. For this reason, the position of an antigen can be determined from the fluorescence intensity distribution.

In this field of art, a strong demand has recently arisen for studies of more precise antibody distributions by observing substances smaller than about 1 µm. At present, successful realization of this depends upon the use of an electron microscope. In observations using electron microscopes, images are observed by using the difference in electron beam reflectances or transmittances among various positions of a specimen. Therefore, in observing an antibody with an electron microscope, elements with large atomic weights are utilized. For example, a molecule containing iron or osmium or a colloidal gold granule of about 1 to 100 nm is currently used as a label of the antibody. FIG. 1 schematically illustrates an antibody using a colloidal gold granule as a label, as an example of an antibody having a label. As in FIG. 1, a composite body of protein A 1 and a colloidal gold granule 2 bonds to an antibody 3. By an antigen-antibody reaction, this antibody 3 binds to a corresponding antigen 4. Therefore, by detecting the position of the colloidal gold granule 2 on a specimen, it is possible to determine the position of the antigen. It is also possible to observe two or more kinds of antigens at the same time by bonding two or more types of colloidal gold granules each having a different size to different kinds of antibodies. In this method, however, colloidal granules may overlap each other during the detection, and so a quantitative determination is difficult to make simply by measuring the number of the colloids.

Phosphors consisting of the above organic molecules include polystyrene spheres which have a particle size of several ten nanometers and emit red-, green-, and bluelights, in addition to molecular organic fluorescent dyes. It has been conventionally known that the polystyrene spheres exhibit bright emissions upon being excited with ultraviolet radiation. Unfortunately, the emission ability of an organic phosphor, including this polystyrene sphere, is degraded upon irradiation of ultraviolet radiation or an electron beam, since the molecular bonds of the dye are readily destroyed. In fact, these organic phosphors cannot be put to use in observations of cathode-luminescence images because not only the original luminous efficacy is low but also the emission intensity is degraded too much to make observation repeatedly. Additionally, these organic phosphors lack storage stability, i.e., deteriorate during storage.

In contrast, inorganic phosphors are stable and deteriorate little upon irradiation of ultraviolet radiation and an electron beam. The particle sizes of inorganic phosphors currently being used in industrial applications are about 4 to 7 µm for CRTs, about 3 to 8 µm for fluorescent lamps, and about 3 to 9 µm for X-ray purposes. The reasons why the particle size is set to these values are as follows. That is, most phosphors are used by being coated on a substrate, and the particle sizes as defined above facilitate this coating. A fluorescent screen is observed mainly by the human eye, and a satisfactory resolution can be obtained with particle sizes to this extent. In conventional manufacturing methods, the luminous efficacy can be readily optimized with particle sizes to this extent, while the luminous efficacy decreases with smaller particle sizes.

It is known that the luminous efficacy of an inorganic phosphor decreases if its particle size is decreased by milling or etching using an acid. The reason for this has been considered that the surface of each individual particle is covered with a non-light-emitting layer, and the volume ratio of this non-light-emitting layer to the entire particle increases if the particle size is decreased. In effect, FIG. 6 inserted in "Television Society Technical Reports ED-754", page 21 shows that the luminous efficacy is decreased to about 10 to 50% by decreasing the particle size from 7 µm to about 1 µm in phosphors manufactured by conventional manufacturing methods. When this is extrapolated, no emission can be expected with particle sizes of 100 nm or smaller.

When cathode-luminescence images are observed with an electron microscope, the images are blurred if the afterglow time of a phosphor is long. To obtain clear images, therefore, it is necessary to use a phosphor having as short an afterglow time as possible. It has been conventionally known that a phosphor doped with Eu as a luminescent center, e.g., $Y_2O_3$: Eu, has a high luminous efficacy and is easy to manufacture as a red phosphor. Unfortunately, this phosphor has a relatively long afterglow time up to milliseconds and is therefore unsuitable for observations of cathode-luminescence images.

As discussed above, in observing micro regions by using an electron microscope, it is difficult to perform quantitative measurements if a molecule or a colloidal gold granule containing elements having large atomic weights is used as a labeling agent. If a phosphor is used as the labeling agent instead of these substances, quantitative measurements are possible. However, organic phosphors deteriorate significantly upon irradiation with an electron beam or ultraviolet radiation or during storage. As inorganic phosphors, on the other hand, no phosphors having both a small particle size and a high luminous efficacy have been obtained yet.

Organic phosphors have been conventionally used in fields other than medicine, e.g., in the field of fluorescent inks under ultraviolet irradiation. However, these organic phosphors also have the problem that fluorescent intensity fades with use for long periods of time. For this reason, inorganic phosphors for fluorescent inks, which do not readily deteriorate have been desired. Unfortunately, the particle size of a phosphor for use in an ink is commonly 1 µm or smaller. Therefore, as described above, no inorganic phosphor having both a small particle size and a high luminous efficacy has been obtained yet.

SUMMARY OF THE INVENTION

It is therefore an object of the present invention to provide a specifically binding material which binds specifically to a substance to be measured and is labeled with a labeling agent which can be quantitatively measured, deteriorates little upon irradiation with, e.g., an electron beam or ultraviolet radiation or during storage, and has a sufficient luminous efficacy and a small particle size.

It is another object of the present invention to provide a method of measuring the substance quantity in accordance with a fluorescence intensity using the labeled specifically binding material described above.

It is still another object of the present invention to provide an ultrafine inorganic phosphor which can be suitably used in observation of color cathode-luminescence images or as a fluorescent component of a fluorescent ink under ultraviolet irradiation and has a high luminous efficacy.

A specifically binding material according to the present invention is labeled with an ultrafine inorganic phosphor 1 to 100 nm in particle size. In this specifically binding material of the present invention, the phosphor is preferably one of $$Ln_2O_3:Re, Ln_2O_2S:Re, ZnO, CaWO_4, MO \cdot xAl_2O_3:Eu,$$
$$Zn_2SiO_4:Mn, \text{ and } LaPO_4:Ce,Tb,$$

wherein Ln represents at least one element selected from the group consisting of La, Gd, Lu, and Y, Re represents at least one element selected from the group consisting of lanthanide elements, M represents at least one element selected from the group consisting of alkali earth metals, and x represents a value from 0.5 to 15. The specifically binding material is preferably one of an antigen, an antibody, and a receptor, and a ligand, a probe, and a primer for the receptor.

A method of detecting a substance to be measured according to the present invention comprises the steps of reacting a specifically binding material, which binds specifically to a substance to be measured, with a specimen, removing an unreacted specifically binding material, and detecting the specifically binding material bound to the specimen, wherein the specifically binding material is labeled with an ultrafine inorganic phosphor 1 to 100 nm in particle sizes. As the ultrafine inorganic phosphor for labeling the specifically binding material for use in this method, the above-mentioned ultrafine inorganic phosphor of the present invention can be suitably used.

Furthermore, the ultrafine inorganic phosphor of the present invention, which can be suitably used in observation of color cathode-luminescence images, is represented by the composition $Ln_2O_3:Pr$, $Ln_2O_2S:Pr$, or $CaWO_4$ and has a particle size of 1 nm to 1 μm.

In the present invention, it is possible to obtain a specifically binding material which binds specifically to a substance to be measured and is labeled with a labeling agent which can be quantitatively measured, deteriorates little upon irradiation of, e.g., an electron beam or ultraviolet radiation or during storage, and has a sufficient luminous efficacy and a small particle size. The use of the specifically binding material labeled with the ultrafine inorganic phosphor according to the present invention allows detection of a substance to be measured with a resolution of 1 μm or less and makes simultaneous detection of two or more different types of substances to be measured feasible.

Also, the ultrafine inorganic phosphor according to the present invention deteriorates little under irradiation with, e.g., an electron beam or ultraviolet radiation or during storage and has a sufficient luminous efficacy. Therefore, this ultrafine inorganic phosphor can be preferably used in observation of cathode luminescence or as a fluorescent component of a fluorescent ink under ultraviolet irradiation.

Note that the ultrafine inorganic phosphor relating to the present invention can be applied not only to a labeling agent or fluorescent ink but also to fluorescent chromatography, a dye laser, electrophoresis, a fluorescent brightning agent, a fluorescent lamp, and a phosphor screen of a high-resolution display.

BRIEF DESCRIPTION OF THE DRAWINGS

FIG. 1 is a view schematically showing the reaction between a conventional antibody labeled with a colloidal gold granule and an antigen;

FIG. 2 is a transmission electron micrograph showing the shape of an ultrafine inorganic phosphor manufactured in Example 1 of the present invention;

DETAILED DESCRIPTION OF THE PREFERRED EMBODIMENTS

Figure 3:
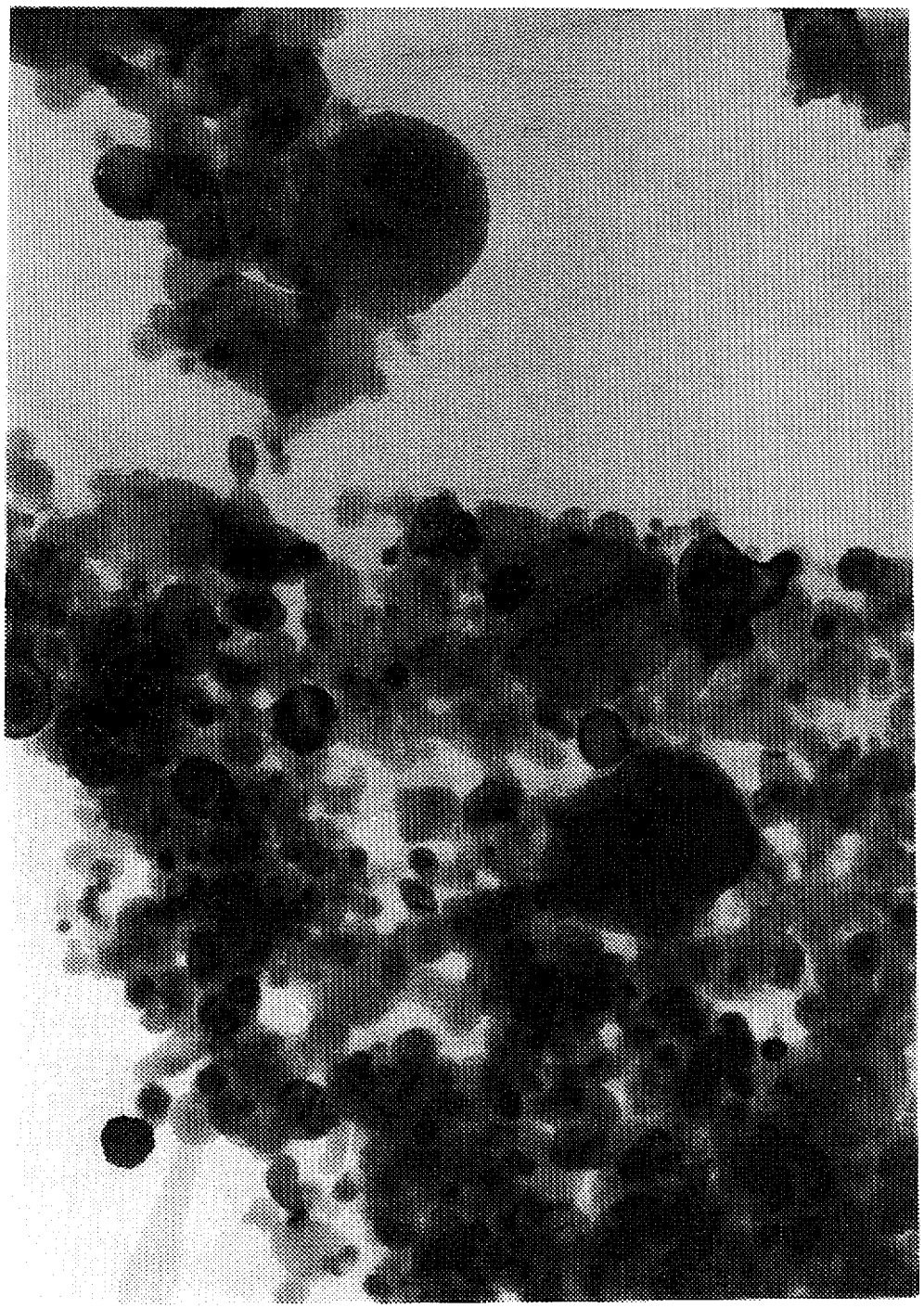
FIG. 3 is a transmission electron micrograph showing the shape of an ultrafine inorganic phosphor manufactured in Example 2 of the present invention.

An inorganic phosphor of oxide with a particle size of 1 nm to 1 μm, preferably 1 to 100 nm takes part in the present invention. A preferred example of this inorganic phosphor is a phosphor represented by the composition $Ln_2O_3:Re$, $Ln_2O_2S:Re$, $ZnO$, $CaWO_4$, $MO \cdot xAl_2O_3:Eu$, $Zn_2SiO_4:Mn$, or $LaPO_4:Ce,Tb$, wherein Ln represents at least one element selected from the group consisting of La, Gd, Lu, and Y, Re represents at least one element selected from the group consisting of lanthanide elements, M represents at least one element selected from the group consisting of alkali earth metals, and x represents a value from 0.5 to 15.

These inorganic phosphors of oxide having different compositions are different in the color of fluorescence emitted. An example of a phosphor giving red emission is cubic $Y_2O_3:Pr$. The Pr concentration of this phosphor is preferably 0.01 to 10%.

Examples of a phosphor giving yellow-green emission are monoclinic $Y_2O_3:Pr$ and monoclinic $Gd_2O_3:Pr$ having a peak at, e.g., around a wavelength of 510 nm. The Pr concentration of these phosphors is preferably 0.05 to 10%.

The particle size of these phosphors is 1 nm to 1 μm, preferably 1 to 100 nm. If the particle size is smaller than 1 nm, the luminous efficacy upon irradiation with an electron beam tends to decrease A particle size greater than 1 μm is impractical because the size is too large as a fluorescent component of an ink. When a phosphor is to be used in medical applications, e.g., as a labeling agent, the particle size is preferably 100 nm or smaller.

As a method by which fine particles are obtained, a method of milling large particles has been conventionally known. It is, however, also well known that the luminous efficacy of an inorganic phosphor is decreased by milling. In effect, when an inorganic phosphor fine powder prepared by milling was observed as a cathode-luminescence image, emission was found only in a limited central portion of each fine particle, and no emission was observed in a wide portion surrounding the central portion. Also, fine particles with a uniform shape cannot be obtained by this method.

Therefore, the present inventors have made extensive studies and found that it is possible to obtain an ultrafine inorganic phosphor with a small particle size and a sufficiently high luminous efficacy by manufacturing an inorganic phosphor of oxide having the composition described above by using a method by which fine particles can be prepared directly without being milled. Examples of the method capable of directly preparing fine particles are a process of evaporation in a gas including a radio frequency (RF, at typically 1 MHz–5 GHz) thermal plasma process, direct current thermal plasma spraying, sputtering, glass crystallization, a sol-gel process, precipitation including hydrothermal synthesis, and a thermal spraying process.

A preferred choice of the above preparation processes depends upon the composition of an ultrafine inorganic phosphor to be prepared. For example, of the inorganic phosphors having the above-mentioned compositions, it is preferable to prepare $Ln_2O_3$:Re by the RF thermal plasma process, $Ln_2O_2S$:Re by the RF thermal plasma process or the sputtering, ZnO by the RF thermal plasma process, $CaWO_4$ by the RF thermal plasma process or arc melting, $MO.xAl_2O_3$:Eu by the hydrothermal synthesis, $Zn_2SiO_4$:Mn by the RF thermal plasma process or the hydrothermal synthesis, and $LaPO_4$:Ce,Tb by the RF thermal plasma process or the hydrothermal synthesis.

An ultrafine inorganic phosphor prepared by any of the above processes shows a stable, satisfactory emission even under irradiation with an electron beam or ultraviolet radiation and does not significantly change the color of the emission.

The specifically binding material labeled with the ultrafine inorganic phosphor according to the present invention is a specifically binding material which is labeled with the inorganic phosphor of oxide 1 to 100 nm in particle size discussed above and specifically binds to a substance to be measured.

In the present invention, the specifically binding material means a material which binds specifically to a substance to be measured. Examples of the material are an antigen, an antibody, a receptor, and polynucleotides such as a ligand, a probe and a primer for the receptor.

In the present invention, the particle size of the ultrafine inorganic phosphor as a labeling agent is preferably 1 to 100 nm. As mentioned earlier, if the particle size is smaller than 1 nm, the luminous efficacy upon irradiation with particularly an electron beam tends to decrease. A particle size greater than 100 nm is impractical because the size is too large as a labeling agent for use in the fields of biology and medicine.

A method by which the specifically binding material is labeled with these ultrafine inorganic phosphors is not particularly limited, and so any method commonly used in this field of art can be used. An example is a method of labeling via protein A as in the protein A-gold colloid method. In this method, it is desirable to increase the dispersibility of the ultrafine inorganic phosphor in a solution, and for that purpose it is effective to control the electrification tendency of the surface of a particle. To achieve this objective, it is possible to wash the surface of a particle with an acid or a base or to treat the surface with a surfactant.

Detection and quantitative measurement of a substance to be measured performed by using the specifically binding material labeled with the ultrafine inorganic phosphor according to the present invention can be done as follows. First, a specifically binding material which binds specifically to a substance to be measured is chosen and labeled with a proper ultrafine inorganic phosphor as discussed above. Subsequently, the specifically binding material labeled with the ultrafine inorganic phosphor thus prepared is added to a system in which a specimen exists and reacted under appropriate conditions. The reaction conditions are not particularly limited provided that the substance to be measured and the specifically binding material can react with each other. With this reaction, the specifically binding material binds to the substance to be measured if the substance is present in the specimen. When a predetermined time elapses, the specimen is cleaned to remove any unreacted specifically binding material from the system. Subsequently, the specimen is set in an electron microscope provided with a fluorescence detector in a detection unit, and fluorescence is detected. Consequently, the position of the phosphor, i.e., the position of the specifically binding material bound to the substance to be measured can be detected as a cathodeluminescence image with a resolution of 1 μm or less, and this makes it possible to locate the position of the substance. Additionally, the substance quantity can be determined also by measuring the fluorescence intensity.

Furthermore, as mentioned earlier, inorganic phosphors having different compositions emit fluorescence in different colors. By using this property, different kinds of substances to be measured can be simultaneously detected by labelling two or more specifically binding materials having different selectiveities with ultrafine inorganic phosphors different in colors of emission and by performing measurements in the same fashion as described above. To observe cathodeluminescence images of two or more phosphors different in colors of emission simultaneously, it is possible to use the color fluorescence electron microscopy described in Japanese Electron Microscope Society ed., "Electron Microscopy", page 123.

The present invention will be described in more detail below by way of its examples.

EXAMPLE 1

A $Y_2O_3$:Eu phosphor with a mean particle size of about 1.5 μm was formed by an oxalate coprecipitation method. This phosphor was vaporized by an RF (4 MHz) thermal plasma process and cooled to prepare fine particles. The obtained fine particles were spherical particles with a primary particle size of about 10 to 800 nm. Subsequently, the obtained phosphor particles were suspended in water and left to stand, and then particles with a particle size of 150 nm or more were removed by performing classification by which only the suspended portion was chosen. FIG. 2 shows the transmission electron micrograph of the resultant phosphor particles.

Upon irradiation of an electron beam of 10 kv, the resultant phosphor exhibited a luminous efficacy of about 5 times higher than that of a fine phosphor particle obtained by milling a conventional phosphor. Cathode-luminescence images were observed by using this phosphor. Consequently, no decrease in the emission output was found even after the observation was repeated 10 times or more under the conditions by which a polystyrene organic phosphor (Comparative Example 1 described below) did not emit light any longer when the observation was performed once. Since the afterglow time was relatively long, the image obtained by using the resultant phosphor was slightly blurred.

The output of the phosphor under irradiation of ultraviolet radiation was about 10 times higher than that of a phosphor particle obtained by milling a conventional phosphor. When the phosphor was dispersed in alcohol, sedimentation speed was slow enough to keep the suspension dispersed even for a week, and it was suitable for a fluorescent ink.

EXAMPLE 2

A $Y_2O_3$:Pr phosphor with a mean particle size of 3 μm and a Pr concentration of 0.1 mol % was prepared by an oxalate coprecipitation method. This phosphor was vaporized by an RF thermal plasma process and cooled to prepare fine particles. The obtained fine particles had a primary particle size of 10 to 500 nm. Subsequently, these phosphor particles were suspended in water and left to stand, and particles with a particle size of 100 nm or more were removed by performing classification by which only the suspended portion was chosen. FIG. 3 shows the transmission electron micrograph of the resultant phosphor. It was found from the X-ray diffraction pattern that, though there was a small amount of the cubic crystal phase, this phosphor mainly consisted of the monoclinic phase.

Figure 4:
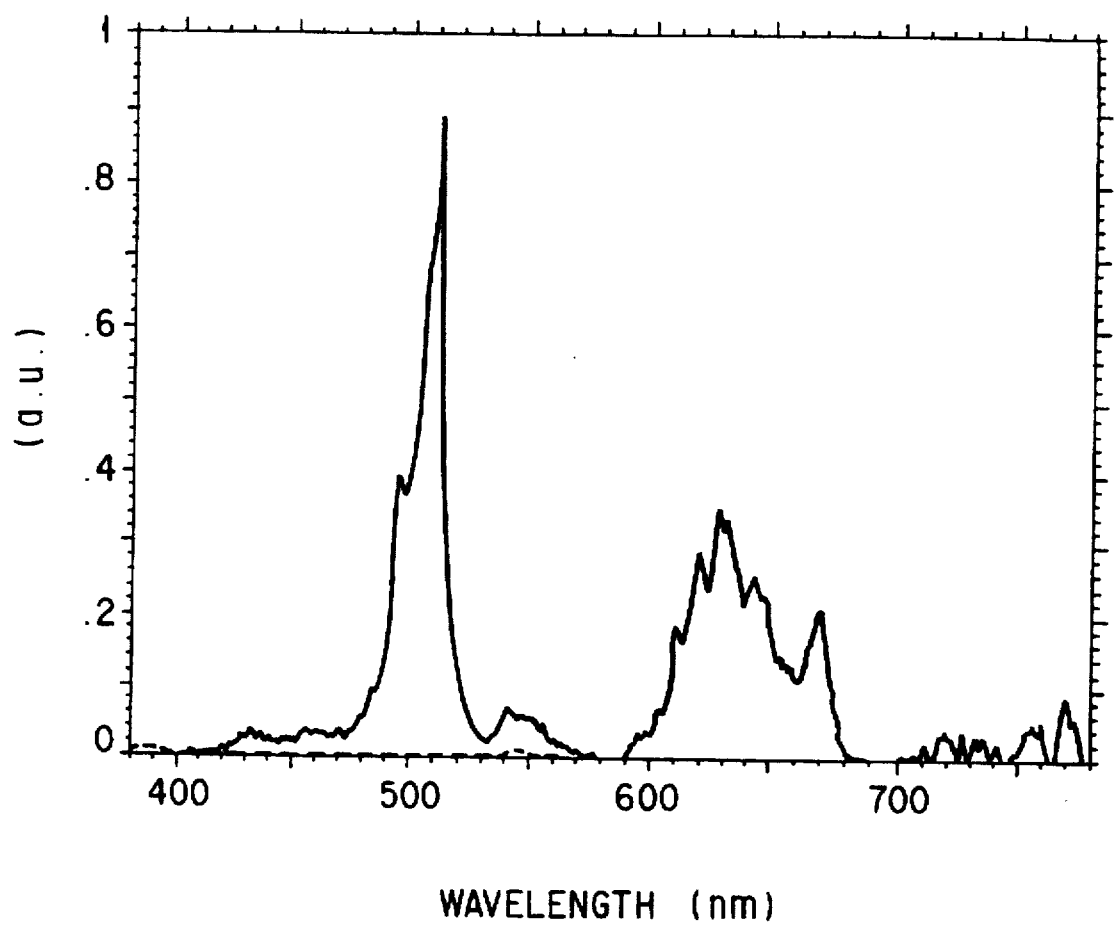
FIG. 4 is a graph showing the emission spectrum under irradiation with an electron beam at 10 kV of the ultrafine inorganic phosphor manufactured in Example 2 of the present invention.

The resultant phosphor gave yellow-green emission upon being irradiated with either ultraviolet radiation or an electron beam of 10 kV. A part of the phosphor, however, gave red emission. On the other hand, the phosphor before the treatment gave only red emission under the same irradiation conditions. FIG. 4 shows the emission spectrum of this phosphor, which obtained under irradiation with an electron beam at 10 kV. The main peak wavelength of the phosphor was 512 nm.

The luminous efficacy of this phosphor was about 5 times as high as that of the fine phosphor powder (Comparative Example 2) obtained by milling a conventional phosphor.

Cathode-luminescence images were observed by using this phosphor. Consequently, no decrease was found in the emission output even after the observation was repeated 10 times or more under the conditions by which the polystyrene organic phosphor (Comparative Example 1) did not emit light any longer when the observation was performed once.

EXAMPLE 3

A commercially available $CaWO_4$ phosphor was vaporized by an RF thermal plasma process and cooled to prepare fine particles. The obtained fine particles were spherical particles with a particle size of 50 to 300 nm. The phosphor was then suspended in water and left to stand, and particles with a particle size of 100 nm or more were removed by performing classification by which only the suspended portion was chosen. It was found by X-ray diffraction that the phosphor contained a trace amount of a $WO_3$ phase.

The resultant phosphor gave blue emission upon irradiation with ultraviolet radiation and excitation with an electron beam, and the respective luminous efficiencies of the phosphor were 5% and 3%, respectively, of that of the phosphor before the treatment.

EXAMPLE 4

A commercially available ZnO phosphor was vaporized by an RF thermal plasma process and cooled to prepare fine particles. The obtained fine particles were classified in alcohol to prepare particles with a mean particle size of 50 nm.

The resultant phosphor gave pale green emission upon being irradiated with either ultraviolet radiation or an electron beam of 10 kv. This pale green emission had an emission spectrum with a peak wavelength at 520 nm. The afterglow time of the phosphor was 200 μsec.

The luminous efficacy of this phosphor was 5 times as high as that of the phosphor fine powder (Comparative Example 2) obtained by milling a conventional phosphor.

Cathode-luminescence images were observed by using this phosphor. Consequently, no decrease was found in the emission output even after the observation was repeated 10 times or more under the conditions by which the polystyrene organic phosphor (Comparative Example 1) did not emit light any longer when the observation was performed once.

EXAMPLE 5

A commercially available $Zn_2SiO_4$:Mn phosphor was vaporized by an RF thermal plasma process and cooled to prepare fine particles. Subsequently, the obtained fine particles were classified in alcohol, preparing particles with a mean particle size of 70 nm.

The resultant phosphor gave green emission upon irradiation with ultraviolet radiation and excitation with an electron beam, and the respective luminous efficiencies of the phosphor were 60% and 40%, respectively, of that of the phosphor before the treatment.

EXAMPLE 6

$BaO.2MgO.8Al_2O_3$:Eu was synthesized by a hydrothermal reaction using an autoclave, thereby preparing tabular particles with a mean diameter of 50 nm and a thickness of 10 nm.

The resultant phosphor gave blue emission upon being excited with ultraviolet radiation. The luminous efficacy of the phosphor was 40% of that of a commercially available phosphor with the same composition.

EXAMPLE 7

$LaPO_4$:Ce,Tb was synthesized by a hydrothermal reaction using an autoclave, thereby preparing particles with a mean diameter of 80 nm.

The resultant phosphor gave green emission upon being excited with ultraviolet radiation. The luminous efficacy of the phosphor was 60% of that of a commercially available phosphor with the same composition.

EXAMPLE 8

Sputtering was performed in argon in a low degree of vacuum by using a commercially available $Y_2O_2S$:Eu phosphor for a color TV system as a target, producing fine particles on an aluminum foil. The obtained fine particles were collected and found to have a mean diameter of 30 nm. It was possible by using these fine particles to observe cathode-luminescence images repeatedly.

EXAMPLE 9

A composite body was manufactured by using the phosphor manufactured in Example 2, in place of a gold colloid, in a protein A-gold colloid composite body manufacturing method. That is, the phosphor fine powder prepared in Example 2 was suspended in water, and protein A was mixed in the suspension. Thereafter, centrifugal sedimentation was performed to obtain a protein A-phosphor composite body.

After the antigen-antibody reaction was done between an antibody labeled with the protein A-phosphor composite body and a specimen having an antigen, it was possible to observe cathode-luminescence images. Also, even after the observation was repeatedly made, no decrease was found in the emission output unlike when organic phosphors were used.

EXAMPLE 10

The phosphors manufactured in Examples 2, 3, and 4 discussed above were bound to three types of antibodies for three types of antigens, respectively. Subsequently, antigen-antibody reactions were caused between these phosphor-labeled antibodies and a specimen having the above three types of antigens. Thereafter, cathode-luminescence images were observed.

Consequently, it was possible to separately observe sites giving yellow-green, blue, and pale green emissions. In addition, even after the observation was carried out repeatedly, no decrease was found in the emission output unlike when organic phosphors were used.

Comparative Example 1

Cathode-luminescence images of red-fluorescent polystyrene spheres (BIOCLEAN FLUORESCENT MICRO-BEADS AR100 (tradename) available from Duke Corp.) with a mean particle size of 100 nm were observed under the same conditions as in Example 1.

Consequently, the luminous intensity was 1/30 or less compared to that in Example 1 and decreased to 1/10 or less of that value when the measurement was performed once.

Comparative Example 2

Fine particles with a mean particle size of about 100 nm were obtained by milling a ZnS:Cu phosphor capable of green emission. The luminous efficacy of the obtained fine particles was measured under irradiation with ultraviolet radiation or an electron beam Consequently, the luminous efficacy was less than 1%, a very small value compared to that in Example 2.

EXAMPLE 11

A $Gd_2O_3$:Pr phosphor with a mean particle size of 3 μm and Pr concentration of 0.1 mol % was prepared by an oxalate coprecipitation method. This phosphor was vaporized by an RF thermal plasma process and cooled to prepare fine particles. The obtained fine particles had a primary particle size of 10 to 800 nm. Subsequently, this phosphor was suspended in water and left to stand, and particles with a particle size of 100 nm or more were removed by performing classification by which only the suspended portion was chosen. It was found from the X-ray diffraction pattern that the crystal system of this phosphor was a monoclinic system.

The resultant phosphor gave yellow-green emission upon being irradiated with either ultraviolet radiation or an electron beam of 10 kV. On the other hand, the phosphor before the treatment exhibited red emission under the same irradiation conditions.

The luminous efficacy of this phosphor was 5 times as high as that of the phosphor fine powder (Comparative Example 2) obtained by milling a conventional phosphor.

Cathode-luminescence images were observed by using this phosphor. Consequently, no decrease was found in the emission output even after the observation was repeated 10 times or more under the conditions by which the polystyrene organic phosphor (Comparative Example 1) did not emit light any longer when the observation was performed once.

EXAMPLE 12

A $Y_2O_3$:Pr phosphor with a mean particle size of 3 μm and Pr concentration of 0.1 mol % was prepared by an oxalate coprecipitation method. This phosphor was vaporized by the direct-current thermal plasma spraying and instantaneously cooled by releasing into water, thereby preparing fine particles. The obtained fine particles had a primary particle size of 50 nm to 1 μm. It was found from the X-ray diffraction pattern that the main crystal system of this phosphor was a monoclinic system.

The resultant phosphor gave yellow-green emission upon being irradiated with either ultraviolet radiation or an electron beam of 10 kv. On the other hand, the phosphor before the treatment exhibited red emission under the same irradiation conditions.

The luminous efficacy of this phosphor was 4 times as high as that of the phosphor fine powder (Comparative Example 2) obtained by milling a conventional phosphor.

Cathode-luminescence images were observed by using this phosphor. Consequently, no decrease was found in the emission output even after the observation was repeated 10 times or more under the conditions by which the polystyrene organic phosphor (Comparative Example 1) did not emit light any longer when the observation was performed once.

EXAMPLE 13

A $Y_2O_3$:Pr phosphor with a mean particle size of 3 μm and Pr concentration of 0.1 mol % was prepared by an oxalate coprecipitation method. This phosphor was vaporized by an RF thermal plasma process and cooled to prepare fine particles. The obtained fine particles had a primary particle size of 10 to 800 nm. Subsequently, this phosphor was heated at 800 to 900° C. for 30 minutes. The phosphor was then suspended in water and left to stand, and particles with a particle size of 100 nm or more were removed by classification by which only the suspended portion was chosen. It was found from the X-ray diffraction pattern that the crystal system of this phosphor was a cubic system.

The resultant phosphor gave red emission upon being irradiated with either ultraviolet radiation or an electron beam of 10 kv.

The luminous efficacy of this phosphor was 5 times as high as that of the phosphor fine powder (Comparative Example 2) obtained by milling a conventional phosphor. The afterglow time of the phosphor was 200 μsec.

Cathode-luminescence images were observed by using this phosphor. Consequently, no decrease was found in the emission output even after the observation was repeated 10 times or more under the conditions by which the polystyrene organic phosphor (Comparative Example 1) did not emit light any longer when the observation was performed once.

EXAMPLE 14

A $Gd_2O_3$:Pr phosphor with a mean particle size of 3 μm and Pr concentration of 0.1 mol % was prepared by an oxalate coprecipitation method. This phosphor was vaporized by the direct-current thermal plasma spraying and instantaneously cooled by releasing into water, thereby preparing fine particles. The obtained fine particles had a primary particle size of 10 to 500 nm. Subsequently, this phosphor was heated at 800 to 900° C. for 30 minutes. The phosphor was then suspended in water and left to stand, and particles with a particle size of 100 nm or more were removed by classification by which only the suspended portion was chosen. It was found from the X-ray diffraction pattern that the crystal system of this phosphor was a cubic system.

The resultant phosphor gave red emission upon being irradiated with either ultraviolet radiation or an electron beam of 10 kv.

The luminous efficacy of this phosphor was 5 times as high as that of the phosphor fine powder (Comparative Example 2) obtained by milling a conventional phosphor. The afterglow time of the phosphor was 180 μsec.

Cathode-luminescence images were observed by using this phosphor. Consequently, no decrease was found in the emission output even after the observation was repeated 10 times or more under the conditions by which the polystyrene organic phosphor (Comparative Example 1) did not emit light any longer when the observation was performed once.

EXAMPLE 15

A commercially available $Gd_2O_2S$:Pr phosphor for a CRT was vaporized by an RF thermal plasma process and cooled to prepare fine particles. Subsequently, the obtained fine particles were classified in alcohol, preparing particles with a mean particle size of 50 nm.

The resultant phosphor gave green emission upon being irradiated with ultraviolet radiation or an electron beam. The intensity of the green emission emitted in each case was 5 and 10 times as high as that emitted from a phosphor obtained by milling, respectively.

The afterglow time of this phosphor was short. It was possible, therefore, to obtain clear cathode-luminescance images by using the phosphor.

EXAMPLES 16–20

Following the same procedures as in Example 9, protein A-phosphor composite bodies were manufactured by using the phosphors manufactured in Examples 11 to 15, in place of a gold colloid.

After the antigen-antibody reaction was done between each of antibodies labeled with these protein A-phosphor composite bodies and a specimen having an antigen, it was possible to observe cathode-luminescence images. Also, even after the observation was repeatedly made, no decrease was found in the emission output unlike when organic phosphors were used.

What is claimed is:

1. A method for manufacturing an ultrafine inorganic phosphor having a particle size of 1 to 100 nm, comprising the steps of:

vaporizing inorganic phosphor material by thermal plasma processing;

cooling the vaporized material to provide an ultrafine inorganic phosphor in the form of particles, and heat-treating said particles said phosphor material being selected from the group consisting of $Ln_2O_3$: Re, $Ln_2O_2S$: Re, ZnO, $CaWO_4$, $MO.xAl_2O_3$: Eu, $Zn_2SiO_4$: Mn, and $LaPO_4$: Ce, Tb, wherein Ln represents at least one element selected from the group consisting of La, Gd, Lu, and Y, Re represents at least one element selected from the group consisting of lanthanide elements, M represents at least one element selected from the group consisting of alkali earth metals, and x represents a value of from 0.5 to 15;

wherein said ultrafine phosphor has a light output under electron beam excitation sufficient to be detected under cathode-luminescent image observation.

2. The method according to claim 1, wherein said phosphor material is selected from the group consisting of $Y_2O_3$:Eu, $Y_2O_3$:Pr, $CaWO_4$, ZnO, $Zn_2SiO_4$:Mn, $BaO.2MgO.8Al_2O_3$:Eu, $LaPO_4$:Ce, Tb, and $Y_2O_3S$:Eu.

3. The method according to claim 1, wherein said heat-treating step comprises heating said particles at 800 to 900° C. for 30 minutes.

* * * * *